United States Patent
Harsini et al.

(10) Patent No.: US 12,035,871 B1
(45) Date of Patent: Jul. 16, 2024

(54) SHOE SANITIZING MAT

(71) Applicants: Hedayat Harsini, Phoenix, AZ (US); Ronald Perry, Scottsdale, AZ (US)

(72) Inventors: Hedayat Harsini, Phoenix, AZ (US); Ronald Perry, Scottsdale, AZ (US)

( * ) Notice: Subject to any disclaimer, the term of this patent is extended or adjusted under 35 U.S.C. 154(b) by 23 days.

(21) Appl. No.: 17/240,870

(22) Filed: Apr. 26, 2021

(51) Int. Cl.
| A47L 23/02 | (2006.01) |
| A47G 27/02 | (2006.01) |
| A47L 23/26 | (2006.01) |
| A61L 2/10  | (2006.01) |
| A61L 2/26  | (2006.01) |

(52) U.S. Cl.
CPC ............. *A47L 23/02* (2013.01); *A47G 27/02* (2013.01); *A47L 23/266* (2013.01); *A61L 2/10* (2013.01); *A61L 2/26* (2013.01); *A61L 2202/11* (2013.01); *A61L 2202/17* (2013.01)

(58) Field of Classification Search
CPC .......... A47L 23/02; A47L 23/266; A61L 2/10; A61L 2/26; A61L 2202/11; A61L 2202/17; A47G 27/02
See application file for complete search history.

(56) References Cited

U.S. PATENT DOCUMENTS

| 6,602,212 | B1 * | 8/2003 | Ahn ................... A61H 33/6057 |
| | | | 4/541.6 |
| 7,798,159 | B2 * | 9/2010 | Palfy .................... A61C 17/036 |
| | | | 134/184 |
| 7,875,869 | B1 | 1/2011 | Shadan |
| 7,918,229 | B2 | 4/2011 | Cumbie |
| 8,241,565 | B1 | 8/2012 | Abdul |
| 8,624,202 | B2 | 1/2014 | Gil |
| 8,696,985 | B2 | 4/2014 | Gil |
| 8,921,813 | B2 | 12/2014 | Palmer |
| 8,973,197 | B2 | 3/2015 | Omidi |
| 9,101,260 | B2 | 8/2015 | Desu-Kalyanam |
| 9,198,991 | B2 | 12/2015 | Dombrowsky |
| 9,272,058 | B1 | 3/2016 | Montgomery |
| 9,968,238 | B2 | 5/2018 | Patel |
| 10,064,966 | B2 | 9/2018 | Kassel |
| 10,117,958 | B2 | 11/2018 | Dombrowsky |
| 10,765,769 | B2 * | 9/2020 | Eidman ................ A47L 23/263 |
| 2008/0310996 | A1 | 12/2008 | Kim |
| 2009/0314308 | A1 | 12/2009 | Kim |
| 2010/0193709 | A1 | 8/2010 | Dalton |
| 2014/0305470 | A1 * | 10/2014 | Desu-Kalyanam ... A47L 23/263 |
| | | | 134/6 |

(Continued)

*Primary Examiner* — Regina M Yoo

(74) *Attorney, Agent, or Firm* — QuickPatents; Kevin Prince

(57) ABSTRACT

A mat for removing debris and sanitizing the shoes of a person comprises a base that has a bottom side adapted for laying on a floor surface, a top side, two side edges, a front edge, and a rear edge. The top side of the base has a pair of shoe cleaning spaces that may contain recesses therein that each defines a recess side edge. A sanitizing circuit includes a power source, one or more UV sanitizing lamps each disposed for illuminating the person's shoes within one of the shoe recesses, and a switch for applying power to the UV sanitizing lamps. As such, when the person stands with his shoes in the shoe recesses and activates the switch, the UV sanitizing lamps activate to sanitize the person's shoes, and particularly the bottom sole of the shoes and the sides of the shoes.

17 Claims, 6 Drawing Sheets

(56) References Cited

U.S. PATENT DOCUMENTS

| | | |
|---|---|---|
| 2015/0132183 A1* | 5/2015 | Dombrowsky ........... A61L 2/10 |
| | | 422/24 |
| 2016/0175896 A1* | 6/2016 | Montgomery .......... A47L 23/00 |
| | | 250/454.11 |
| 2017/0000915 A1 | 1/2017 | Cottone |
| 2018/0132697 A1 | 5/2018 | Desu-Kalyanam |
| 2019/0117813 A9 | 4/2019 | Dayton |
| 2020/0281444 A1* | 9/2020 | Desu-Kalyanam ......................... |
| | | A46B 13/023 |
| 2020/0390918 A1* | 12/2020 | Eidman ..................... A61L 2/10 |

* cited by examiner

SHOE SANITIZING MAT

CROSS-REFERENCE TO RELATED APPLICATIONS

Not Applicable.

STATEMENT REGARDING FEDERALLY SPONSORED RESEARCH AND DEVELOPMENT

Not Applicable.

FIELD OF THE INVENTION

This invention relates to the combination of debris removal and sanitizing devices, and more particularly to a shoe-sanitizing floor mat.

BACKGROUND

Shoes are notoriously dirty, typically being pressed down on all manner of grime and debris while being used throughout the day. Often shoes can pick-up pathogens that are then brought into a person's home and transferred to carpets and floor surfaces. As such, it would be beneficial to have a device that allows a user to remove debris and to sanitize his shoes before entering his home or work environment.

Any such device will necessarily have a time requirement for a sterilization process to be completed, yet often people do not wait for the sanitization process to complete.

Accordingly, there would be a benefit to a device that alerts a manager or owner of a property if shoes of a visitor were not properly sanitized.

Therefore, there is a need for a device that allows for the quick debris removal and sanitation of a person's shoes, including the bottom sole area of the shoes and the sides of the shoes. Such a needed device would further provide for alerting an authority if a shoe sanitation cycle is not fully completed, or not even properly begun. Such a needed invention would be adaptable to various sized entryways and doorways, and would provide for various messages on interchangeable mat cushions. The present invention accomplishes these objectives.

SUMMARY OF THE INVENTION

The present device is a mat for a combination of debris removal and sanitizing the shoes of a person and for laying on a floor surface. The mat comprises a base that has a bottom side adapted for laying on the floor surface, a top side, two side edges, a front edge, and a rear edge. In some embodiments the front edge and rear edge of the mat each include a sloping ramp section. Some embodiments include a modular mat extension or a modular mat ramp, fixable with either the front edge or rear edge of the mat at a coupler. Some embodiments include sticky mats for fine and complete debris removal.

The top side of the base has a pair of cleaning areas for each shoe that may contain recesses therein. Each shoe cleaning area may define a shoe recess side edge that is angled less than 90-degrees with respect to the shoe recess. The shoe recess side edges each have a reflective surface.

A sanitizing circuit includes a power source, one or more UV sanitizing lamps each disposed for illuminating the person's shoes within one of the shoe recesses, and a switch for applying power to the UV sanitizing lamps. The power source is preferably an AC adapter.

Preferably the UV sanitizing lamps are located under the shoe recesses, the shoe recesses made from a non-opaque material such as polycarbonate or transparent acrylic. As such, UV light produced by the UV sanitizing lamps illuminates a bottom of the shoes and is reflected off of the shoe recess side edges to illuminate a side of the shoes.

Preferably the sanitizing circuit includes a timer, such that when the switch is closed the UV sanitizing lamps are activated for a predetermined activation time, such as 10 seconds, after which the UV sanitizing lamps are deactivated. In such an embodiment, the switch is preferably a momentary contact switch, and the sanitizing circuit further includes an LED indicator, or other visual indicator, that provides a visual countdown indicator representing a remaining activation time of the UV sanitizing lamps. In some embodiments the switch is a pressure switch adapted for detecting the person standing on one of the shoe recesses or on the top surface of the base. In embodiments having the sloping ramp section, the pressure switch may be adapted for detecting the person standing on or depressing the sloping ramp section. In some embodiments there are instructional words or graphics to guide the user through the process of wiping his feet, placing his feet into the cleaning area, and then entering the building once the cleaning cycle has been completed.

As such, when the person stands with his shoes in the cleaning area and activates the switch, the UV sanitizing lamps activate to sanitize the person's shoes, and particularly the bottom sole of the shoes and the sides of the shoes.

In some embodiments, the sanitizing circuit further includes a wireless communication module, a microprocessor, a memory, and supporting circuitry. When the switch is closed and after the UV sanitizing lamps are deactivated, a sanitizing status alert of a person's shoes is transmitted through the wireless communication module to a wireless network to a recipient, such as a smart phone running a software application that receives alerts from the mat and displays them on the smart phone until the alert is dismissed.

The present invention is a device that allows for the quick debris removal and sanitation of a person's shoes, including the bottom sole area of the shoes and the sides of the shoes. The present device further provides for alerting an authority if a shoe sanitation cycle was not fully completed, or not even properly begun. The present invention is adaptable to various sized entryways and doorways, and provides for various messages on interchangeable mat cushions. Other features and advantages of the present invention will become apparent from the following more detailed description, taken in conjunction with the accompanying drawings, which illustrate, by way of example, the principles of the invention.

DETAILED DESCRIPTION OF THE PREFERRED EMBODIMENT

Illustrative embodiments of the invention are described below. The following explanation provides specific details for a thorough understanding of and enabling description for these embodiments. One skilled in the art will understand that the invention may be practiced without such details. In other instances, well-known 6 structures and functions have not been shown or described in detail to avoid unnecessarily obscuring the description of the embodiments.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number, respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list. When the word "each" is used to refer to an element that was previously introduced as being at least one in number, the word "each" does not necessarily imply a plurality of the elements, but can also mean a singular element.

Figure 1A:
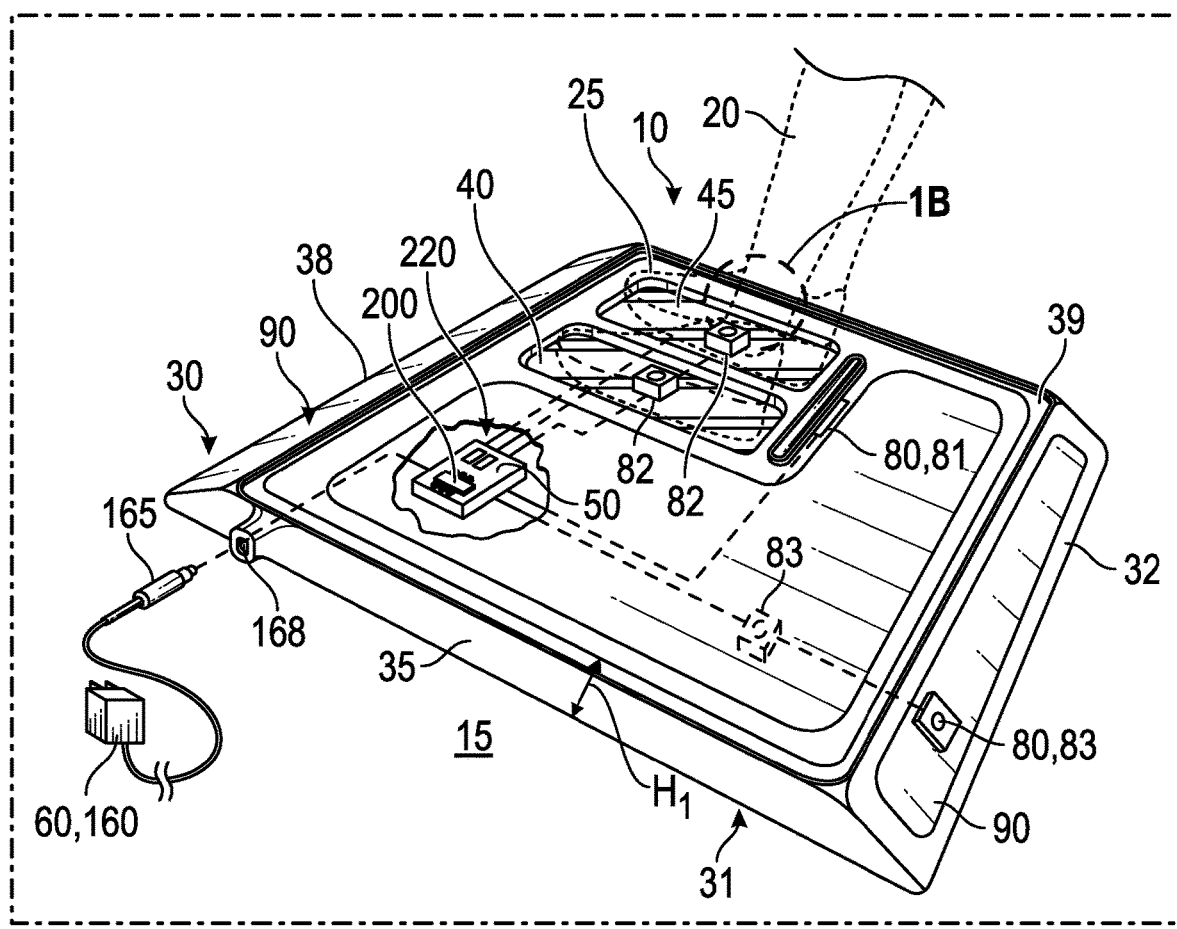
FIG. 1A is a perspective view of one embodiment of the invention, partially broken away to reveal a sanitizing circuit.
Figure 1B:
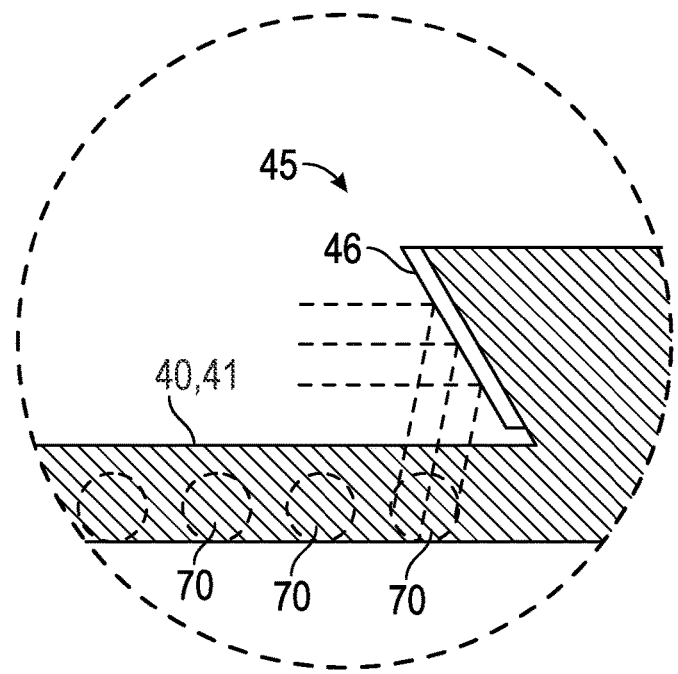
FIG. 1B is a partial cross-sectional view, taken along line 1B-1B of FIG. 1A.
Figure 2:
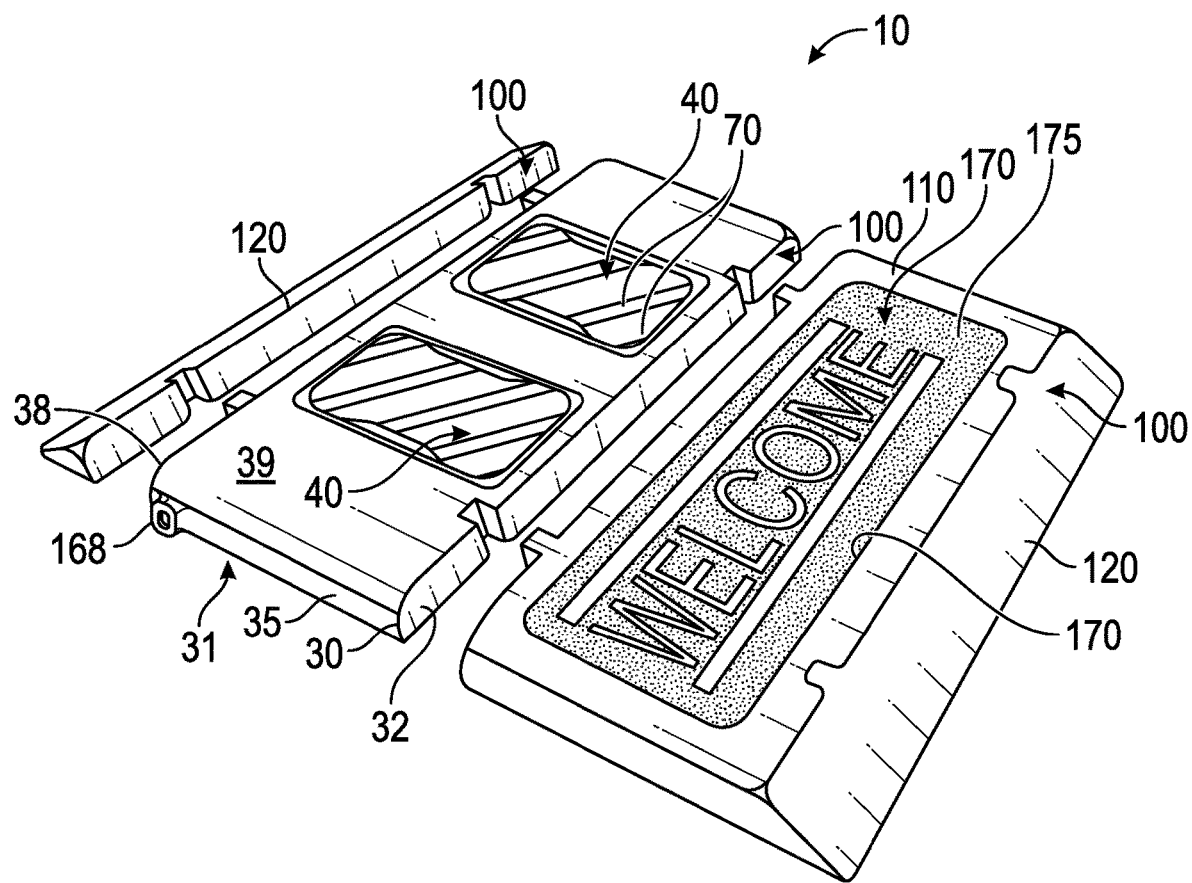
FIG. 2 is a partially exploded perspective view of an alternate embodiment of the invention.

FIGS. 1A, 1B and 2 illustrate a mat for sanitizing the shoes 25 of a person 20 and for laying on a floor surface 15, typically in front of a door (not shown), entryway, or the like. The mat 10 comprises a base 30 that has a bottom side 31 adapted for laying on the floor surface 15, a top side 39, two side edges 35, a front edge 32, and a rear edge 38.

In some embodiments the front edge 32 and rear edge 38 of the mat 30 each include a sloping ramp section 90 transitioning from a floor height to a base height $H_1$ (FIG. 1A). Some embodiments include a modular mat extension 110 or a modular mat ramp 120 (FIG. 2), fixable with either the front edge 32 or rear edge 38 of the mat 30 at a coupler 100. Such a coupler 100 may be a mechanical tab-and-slot arrangement as illustrated, or other suitable mechanical fastening mechanisms such as a hook-and-loop type fastener 11 material (not shown).

The top side 39 of the base 30 may also include an interchangeable mat cushion recess adapted for receiving one of a plurality of mat cushions 175, which are preferably machine washable and adapted to receive a customizable message 176 thereon. Such a mat cushion 175 allows the person 20 to perform an initial scraping-off of debris and grime before starting the sanitation process. Brush bristles (not shown) may be further included to a top side of the mat cushion 175 to further aid the person to scrape-off debris from his shoes 25. As such, the mat cushions 175 may be interchanged to display seasonal greeting messages 176, or the like. Each side edge 35 of the base 30 may also include an elastomeric handle 180, or a handle made of any other suitable material that will not likely scratch the floor surface 15 or break if stepped on inadvertently. Preferably the base 30 is made with a foam material.

Figure 3:
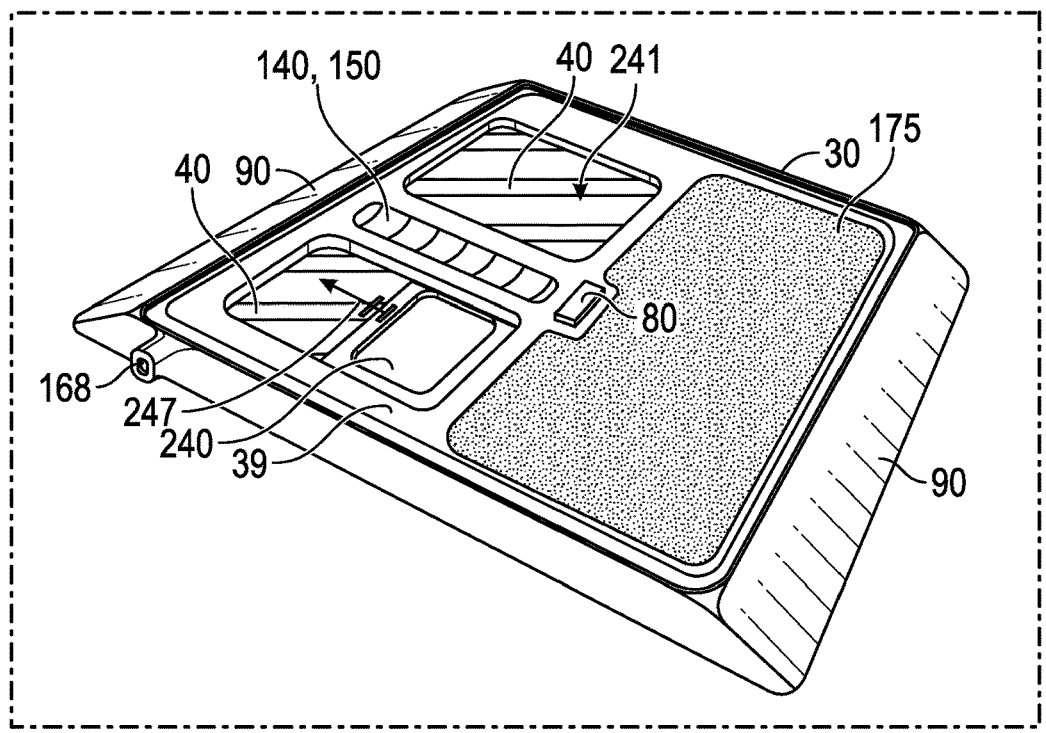
FIG. 3 is a perspective view of another alternate embodiment of the invention.
Figure 4:
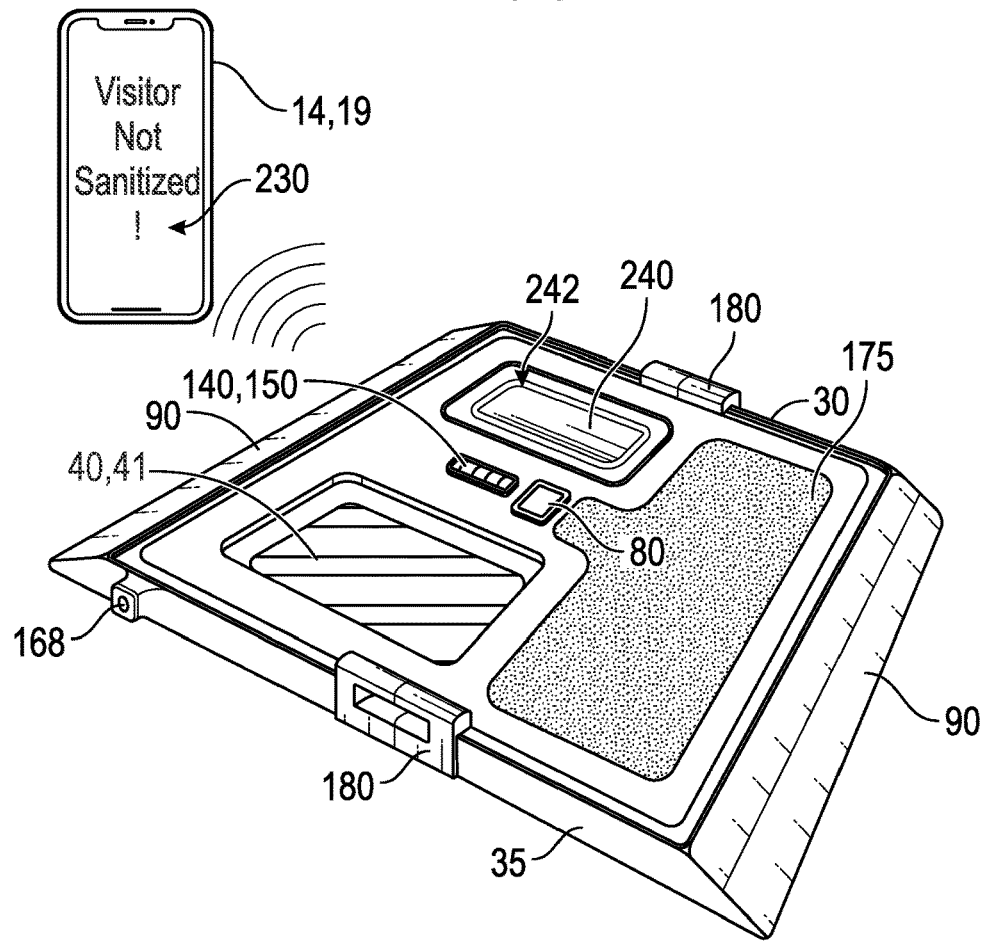
FIG. 4 is a perspective view of yet another alternate embodiment of the invention.
Figure 6:
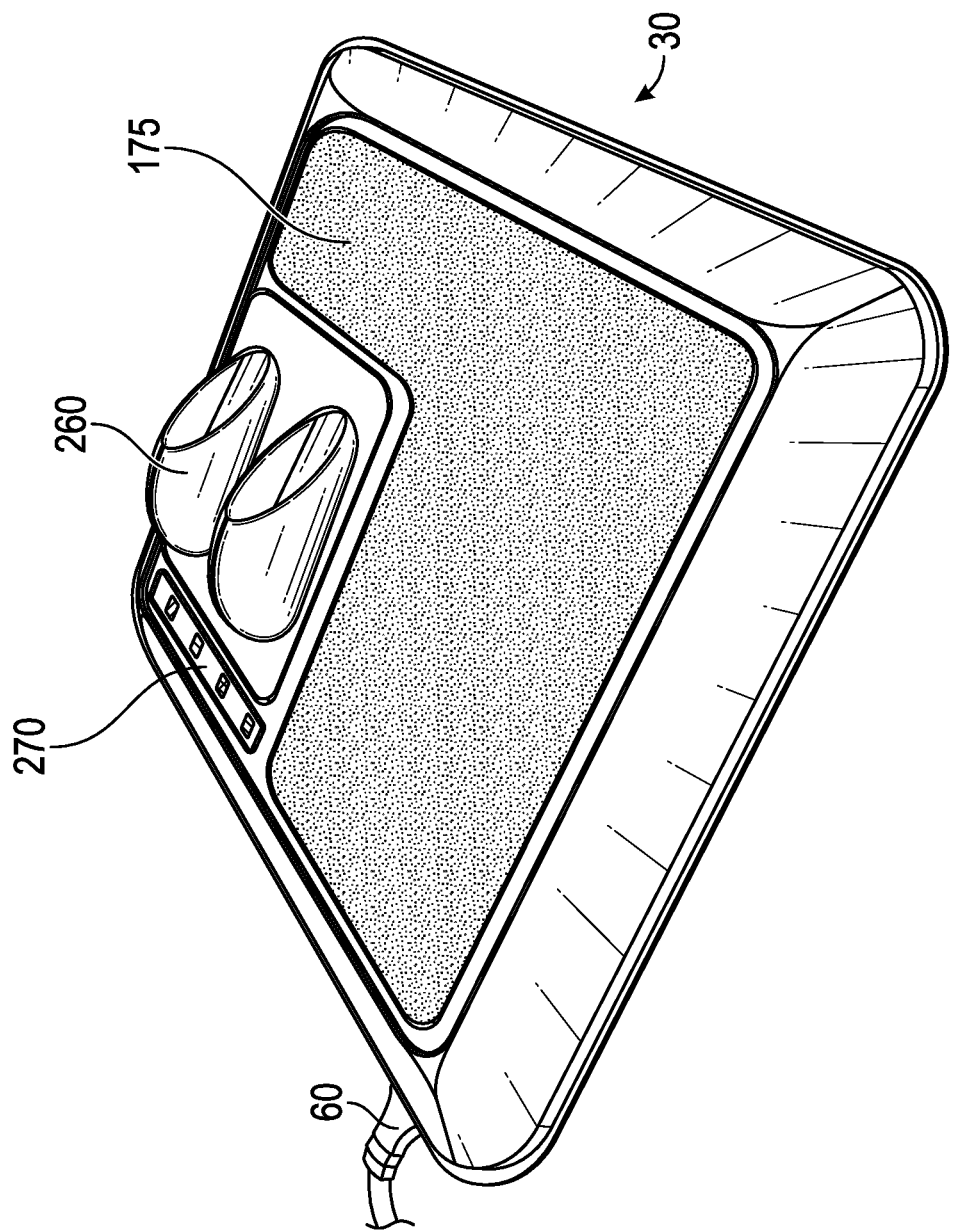
FIG. 6 is a perspective view of still yet another alternate embodiment of the invention that includes a shoe pod and a single shoe recess.
Figure 7:
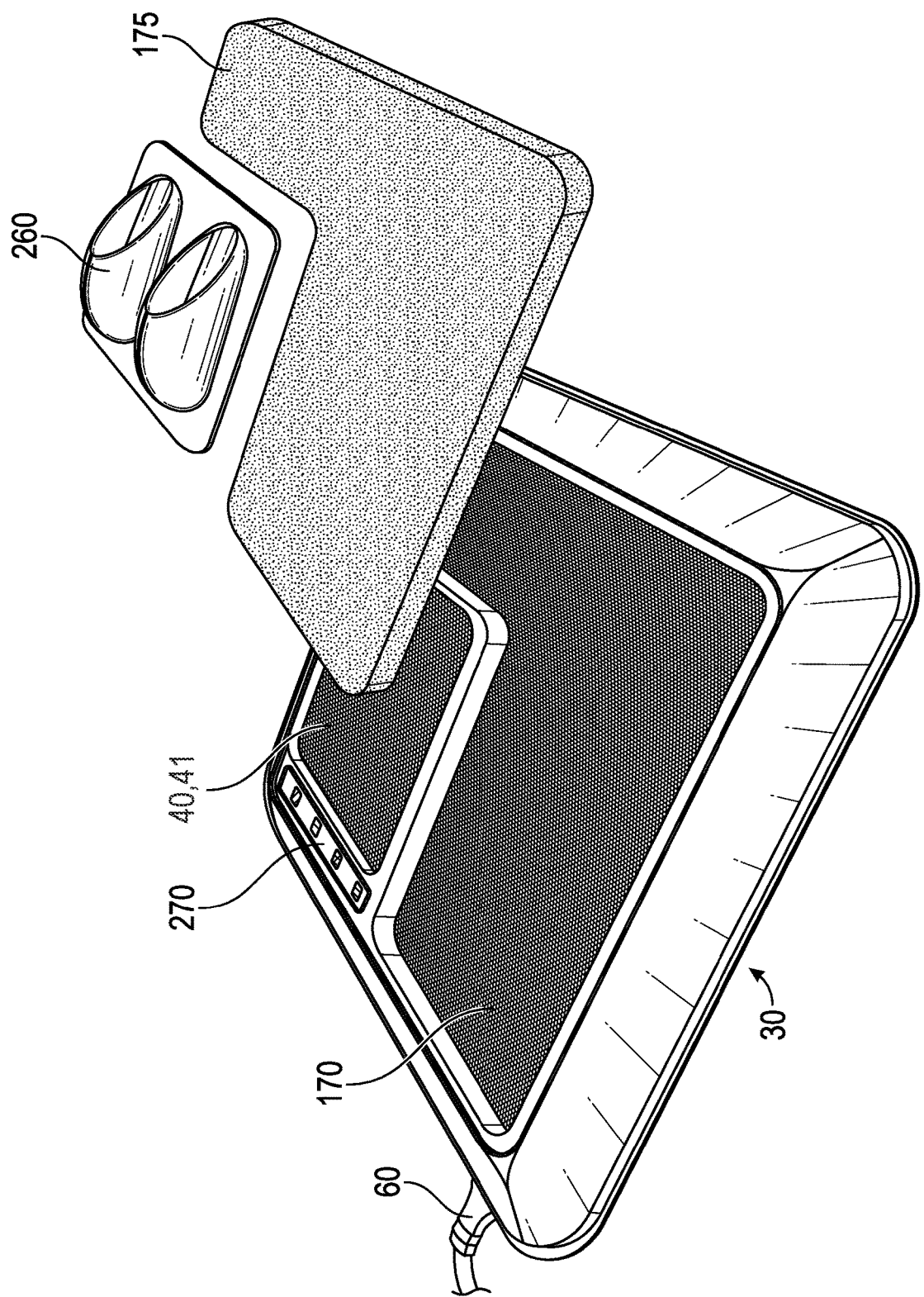
FIG. 7 is an exploded perspective view of the embodiment of FIG. 6.

The top side 39 of the base 30 has one or more shoe spaces 41, each preferably including a recess 40 therein. Each shoe recess 40 defines a shoe recess side edge 45 (FIG. 1B) that is angled less than 90-degrees with respect to the shoe recess 40, such as preferably between 30-degrees to 60-degrees. The shoe recess side edges 45 each have a reflective surface 46. In some embodiments, each shoe recess includes a slidable cover 240 fixed within the base 30 and adapted to move between an open position 241 (FIG. 3) and a closed position 242 (FIG. 4). In some embodiments, the mat 10 includes a single shoe recess 40 and the person 20 places both shoes 25 in the single shoe recess 40. In such an embodiment, a shoe pod 260 (FIGS. 6 and 7) may be included, the shoe pod 260 being translucent or transparent on a lower side thereof, such that light may be transmitted through the lower side of the shoe pod 260 to the shoes 25 therein. For eye safety, such a shoe pod 260 includes an opaque top surface that prevents light from escaping above the shoe pod 260.

A sanitizing circuit 50 includes a power source 60, one or more UV sanitizing lamps 70 such as Ultraviolet-C type UV lamps 70, each disposed for illuminating the person's shoes 25 within one of the shoe recesses 40, and a switch 80 for applying power to the UV sanitizing lamps 70. The power source 60 is preferably an AC adapter 160 plugged into a standard wall outlet and having an AC adapter plug 165 (FIG. 1A) that engages an AC adapter port 168 of the base 30, which is electrically connected with the sanitizing circuit 50.

Preferably the UV sanitizing lamps 70 are located under the shoe recesses 40, the shoe recesses made from a non-opaque material such as polycarbonate or transparent acrylic. As such, UV light produced by the UV sanitizing lamps 70 illuminates a bottom of the shoes 25 and is reflected off of the shoe recess side edges 45 to illuminate a side of the shoes 25. The UV sanitizing lamps 70 are preferably UVC LEDs.

Figure 5:
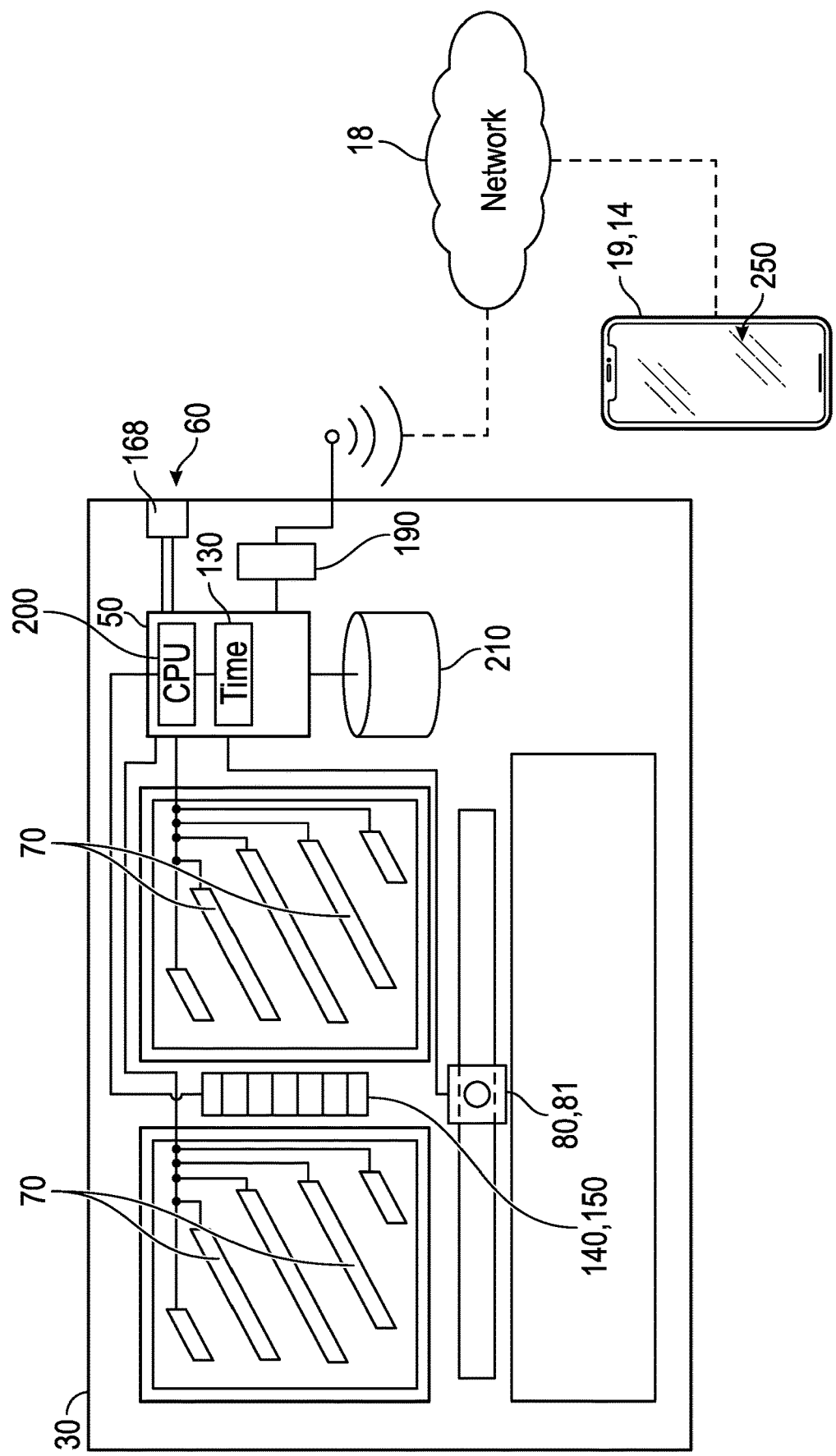
FIG. 5 is a diagram of components of the invention and a system in which the invention 19 is used.

Preferably the sanitizing circuit 50 includes a timer 130 (FIG. 5), such that when the switch 80 is closed the UV sanitizing lamps 70 are activated for a predetermined activation time, such as 10 seconds, after which the UV sanitizing lamps 70 are deactivated. In such an embodiment, the switch 80 is preferably a momentary contact switch 81, and the sanitizing circuit 50 further includes an LED indicator 140, or other visual indicator 140, that provides a visual countdown indicator 150 representing a remaining activation time of the UV sanitizing lamps 70. In some embodiments the switch 80 is a pressure switch 82 adapted for detecting the person 20 standing on one of the shoe recesses 40 or on the top surface 39 of the base 30. In embodiments having the sloping ramp section 90, the pressure switch 82 may be adapted for detecting the person standing on or depressing the sloping ramp section 90.

As such, when the person 20 stands with his shoes 25 in the shoe recesses 40 and activates the switch 80, the UV sanitizing lamps 70 activate to sanitize the person's shoes 25, and particularly the bottom sole of the shoes 25 and the sides of the shoes 25.

In some embodiments, the sanitizing circuit 50 further includes a wireless communication module 190, a microprocessor 200, a memory 210, and supporting circuitry 220. When the switch 80 is closed and after the UV sanitizing lamps 70 are deactivated, a sanitizing status alert 230 of a person's shoes 25 is transmitted through the wireless communication module 190 to a wireless network 18 to a recipient 19, such as a smart phone 14 running a software application 250 that receives alerts from the mat 10 and displays them on the smart phone 14 until the alert 230 is dismissed. Such a wireless network 18 may be a cellular network, the Internet, a Wi-Fi network connected to the Internet, or the like.

In some embodiments, the status alert 230 of the person's shoes 25 is transmitted through the wireless network 18 only if the person 20 removes his shoes 25 from the sanitizing recesses 40 before the predetermined activation time has been reached, alerting an owner of the mat 10 that the person did not complete the sanitizing process. Alternately, the switch 80 of the sanitizing circuit 50 is the pressure switch 81 and is adapted for detecting the person 20 standing on the top surface 39 of the base 30, and the second pressure switch 83 is fixed within at least one of the shoe recesses 40, such that the sanitizing status alert 230 of the person's shoes 25 is transmitted through the wireless network 18 only if the person 20 removes his shoes 25 from the top side 39 of the base 30 without stepping into the sanitizing recesses 40. This again alerts the owner of the mat 10 that the person did not complete the sanitizing process, or even start the sanitizing process.

In some embodiments the LED indicator 140 includes a timeline 270 that shows each step in a sanitation process. As each step is completed, the step is illuminated. For example, the first step may be to step on the mat cushion 175 to wipe-off coarse debris from the person's shoes 25, such step being completed when pressure switch 80 detects the person 20 on the mat cushion 175. As seen in the Figures, the mat cushion 175 may create a planar wiping surface for the person's shoes 25. The next step is to step into the shoe pod 260 to illuminate the person's shoes 25 with the sanitizing UV light from the UV lamps 70 below the shoe recess 40. Such a step is completed when the pressure switch 82 detects the person 20 has stepped into the one or more shoe recesses 40. Then a timing step may be initiated for, say, fifteen seconds. Thereafter the final step is illuminated, to step out of the shoe pod 260, showing the sanitation process is complete.

Light does not escape out of the top side of the shoe pod 260 in such an embodiment, except for perhaps some light escaping out of shoe pod apertures that the person's shoes 25 are inserted into if there is not a tight fit between the shoe pod 260 and the person's shoes 25. In some embodiments, both shoes 25 are inserted into two apertures of a single shoe pod 260. In alternate embodiments, each of two shoe recesses 40 includes a shoe pod 260 having a single shoe aperture (not shown).

While a particular form of the invention has been illustrated and described, it will be apparent that various modifications can be made without departing from the spirit and scope of the invention. For example, while the figures illustrate a generally rectangular base 30, an oval base (not shown) or a base of another shape (not shown) could be utilized, with the front edge 32 merging smoothing into the side edges 35, which themselves could merge into the rear edge 38 smoothly. Or a different number of side edges 35 might be utilized, such as with a hexagon-shaped mat 30. Accordingly, it is not intended that the invention be limited, except as by the appended claims.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention.

The above detailed description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

All of the above patents and applications and other references, including any that may be listed in accompanying filing papers, are incorporated herein by reference. Aspects of the invention can be modified, if necessary, to employ the systems, functions, and concepts of the various references described above to provide yet further embodiments of the invention.

Changes can be made to the invention in light of the above "Detailed Description." While the above description details certain embodiments of the invention and describes the best mode contemplated, no matter how detailed the above appears in text, the invention can be practiced in many ways. Therefore, implementation details may vary considerably while still being encompassed by the invention disclosed herein. As noted 14 above, particular terminology used when describing certain features or aspects of the invention should not be taken to imply that the terminology is being redefined herein to be restricted to any specific characteristics, features, or aspects of the invention with which that terminology is associated.

While certain aspects of the invention are presented below in certain claim forms, the inventor contemplates the various aspects of the invention in any number of claim forms. Accordingly, the inventor reserves the right to add additional claims after filing the application to pursue such additional claim forms for other aspects of the invention.

What is claimed is:

1. A mat for removing debris from and sanitizing a person's shoes and for laying on a floor surface, the mat comprising:

a base having a bottom side adapted for laying on a floor surface, a top side, two side edges, a front edge, and a rear edge, the two side edges being single continuous members spanning between the front edge and the rear edge, the front edge and the rear edge being single, continuous members spanning between the two side edges;

the top side of the base having one or more cleaning spaces adapted for receiving the person's shoes;

a planar wiping surface on the top side of the base, the planar wiping surface being adjacent the one or more cleaning spaces and operable for a user to wipe a bottom surface of the person's shoes;

a sanitizing circuit including a power source, one or more UV sanitizing lamps each disposed within or about the base for illuminating the person's shoes, and a switch for applying power to the one or more UV sanitizing lamps;

whereby with the person standing with the person's shoes in the one or more cleaning spaces and activating the switch, the one or more UV sanitizing lamps activate to sanitize the person's shoes, the mat further including an at least partially non-opaque shoe pod adapted to fit around the person's shoes, the at least partially non-opaque shoe pod having a non-opaque bottom member formed integrally with solid side members, the solid side members extending to meet and form a top surface of the at least partially non-opaque shoe pod, the top surface being opaque to prevent light from exiting above the at least partially non-opaque shoe pod, the non-opaque bottom member, the solid side members and the top surface defining an open space therebetween for receiving the person's shoes, and the planar wiping surface is disposed within the top side of the base and has a size to permit wiping both of the person's shoes manually thereover simultaneously.

2. The mat of claim 1, wherein the front edge and the rear edge of the base each include a sloping ramp section transitioning from a floor height to a base height.

3. The mat of claim 1, wherein the front edge and/or rear edge include a coupler for attaching a modular mat extension or a modular mat ramp.

4. The mat of claim 1, wherein the sanitizing circuit includes a timer, and wherein the switch is a momentary contact switch, wherein after the switch is activated the one or more UV sanitizing lamps are activated for a predetermined activation time, after which the one or more UV sanitizing lamps are deactivated.

5. The mat of claim 4, wherein the sanitizing circuit further includes an LED indicator that, when the switch is activated, displays a visual countdown representing cleaning cycle completion or a remaining activation time of the one or more UV sanitizing lamps.

6. The mat of claim 4, wherein the sanitizing circuit further includes a wireless communication module, a microprocessor, a memory, and supporting circuitry such that a sanitizing status alert of a person's shoes is transmitted through a wireless network to a recipient when the switch is activated and after the one or more UV sanitizing lamps are deactivated.

7. The mat of claim 6, wherein the sanitizing status alert of the person's shoes is transmitted through the wireless network only if the person removes the person's shoes from the one or more cleaning spaces before the predetermined activation time has been reached.

8. The mat of claim 6, wherein the recipient is a software application running on a smart phone.

9. The mat of claim 1, wherein the power source is an AC adapter and wherein the base includes an AC adapter port adapted for receiving an AC adapter plug through which power is delivered to the sanitizing circuit.

10. The mat of claim 1, further comprising a plurality of mat cushions, and wherein the top side includes an interchangeable mat cushion recess adapted for receiving a selected one of the plurality of mat cushions, the selected one of plurality of mat cushions forming the planar wiping surface.

11. The mat of claim 10, wherein the plurality of mat cushions are each machine washable.

12. The mat of claim 10, wherein the plurality of mat cushions are adapted to receive a customizable message thereon.

13. The mat of claim 1, wherein each side edge includes an elastomeric handle.

14. The mat of claim 1, wherein the switch of the sanitizing circuit is a pressure switch adapted for detecting the person standing on the base or one of the one or more shoe cleaning spaces.

15. The mat of claim 1, wherein the front edge and the rear edge of the base each include a sloping ramp section transitioning from a floor height to a base height, and wherein the switch of the sanitizing circuit is a pressure switch adapted for detecting the person standing on the sloping ramp section.

16. The mat of claim 1, wherein the sanitizing circuit further includes an LED indicator that, when the switch is activated, displays steps in a sanitation process and illuminates each step when completed.

17. A mat for removing debris from and sanitizing shoes and for laying on a floor surface, the mat comprising:

a base having a bottom side adapted for laying on a floor surface, a top side, two side edges, a front edge, and a rear edge, the two side edges being single continuous members spanning between the front edge and the rear edge, the front edge and the rear edge being single, continuous members spanning between the two side edges;

the top side of the base having one or more cleaning spaces adapted for receiving a person's shoes;

a sanitizing circuit including a power source, one or more UV sanitizing lamps each disposed within or about the base for illuminating the person's shoes, and a switch for applying power to the one or more UV sanitizing lamps; and a planar wiping surface on the top side of the base, the planar wiping surface being adjacent the one or more cleaning spaces and operable for a user to wipe a bottom surface of the person's shoes;

whereby with the person standing with the person's shoes in the one or more cleaning spaces and activating the switch, the one or more UV sanitizing lamps activate to sanitize the person's shoes, the mat further including an at least partially non-opaque shoe pod adapted to fit around the person's shoes, a top surface of the at least partially non-opaque shoe pod being opaque to prevent light from exiting above the at least partially non-opaque shoe pod, wherein the at least partially non-opaque shoe pod includes an opening for insertion of the person's shoes, the opening permitting a shoe to be inserted into the at least partially non-opaque shoe pod to be covered at least partially by the opaque top surface thereof, the opening permitting the shoe to be inserted in a motion that is co-planar to the top side of the base, the at least partially non-opaque shoe pod having a non-opaque bottom member formed integrally with solid side members, the solid side members extending to meet and form the top surface, the non-opaque bottom member, the solid side members and the top surface defining an open space therebetween for receiving the person's shoes, and the planar wiping surface is disposed within the top side of the base and has a size to permit wiping both of the person's shoes manually thereover simultaneously.

* * * * *